(12) United States Patent
Hogendijk

(10) Patent No.: US 8,002,725 B2
(45) Date of Patent: Aug. 23, 2011

(54) EMBOLIC PROTECTION AND PLAQUE REMOVAL SYSTEM WITH CLOSED CIRCUIT ASPIRATION AND FILTERING

(75) Inventor: Michael Hogendijk, Mountain View, CA (US)

(73) Assignee: NovoStent Corporation, Mountain View, CA (US)

( * ) Notice: Subject to any disclaimer, the term of this patent is extended or adjusted under 35 U.S.C. 154(b) by 42 days.

(21) Appl. No.: 11/184,155

(22) Filed: Jul. 18, 2005

(65) Prior Publication Data
US 2007/0021774 A1    Jan. 25, 2007

(51) Int. Cl.
| | | |
|---|---|---|
| A61M 37/00 | (2006.01) | |
| A61B 1/00 | (2006.01) | |
| A61B 1/12 | (2006.01) | |
| A61M 29/00 | (2006.01) | |
| A61M 1/00 | (2006.01) | |
| A61M 31/00 | (2006.01) | |
| F16K 31/00 | (2006.01) | |
| F16K 1/48 | (2006.01) | |

(52) U.S. Cl. ....... 604/4.01; 600/140; 600/143; 600/156; 600/159; 604/6.16; 604/103.01; 604/103.02; 604/103.08; 604/30; 604/118; 604/119; 604/120; 604/93.01; 251/61.1; 251/335.1; 251/369

(58) Field of Classification Search ............ 604/103.01, 604/103.06, 103.07, 103.13, 103.14, 104, 604/121, 131, 158, 164.03, 164.04, 164.09, 604/164.13, 247, 523, 118–120, 30–35, 6.09, 604/6.1, 6.11, 6.12, 29–34, 103.02, 164.08, 604/6.16; 600/140, 143, 156, 159; 606/113, 606/114, 115, 128, 200, 159, 192; 251/5, 14, 61.1, 335.1, 369
See application file for complete search history.

(56) References Cited

U.S. PATENT DOCUMENTS

| | | | | |
|---|---|---|---|---|
| 2,795,390 A | * | 6/1957 | Laurenty | 251/5 |
| 3,552,712 A | * | 1/1971 | Whitlock | 251/5 |
| 4,268,005 A | * | 5/1981 | Raftis et al. | 251/5 |
| 4,406,656 A | * | 9/1983 | Hattler et al. | 604/523 |
| 4,451,252 A | * | 5/1984 | Martin | 604/43 |
| 4,516,398 A | * | 5/1985 | Wuchinich | 604/22 |
| 4,705,501 A | * | 11/1987 | Wigness et al. | 604/43 |
| 4,894,057 A | * | 1/1990 | Howes | 604/523 |
| 4,923,462 A | | 5/1990 | Stevens | |

(Continued)

FOREIGN PATENT DOCUMENTS

WO    9823319 A1    6/1998

(Continued)

OTHER PUBLICATIONS

Extended EP Search Report from corresponding EP application No. 06787653.2-1526; Apr. 9, 2010; 7 pages.

*Primary Examiner* — Leslie Deak
*Assistant Examiner* — Adam Marcetich
(74) *Attorney, Agent, or Firm* — James F. Mann; Haynes Beffel & Wolfeld LLP

(57) ABSTRACT

Embolic protection and plaque removal apparatus and methods are provided wherein an aspiration device aspirates, filters and reperfuses blood using a closed fluid circuit having a bi-directional working lumen. The plaque removal device includes a plurality of self-expanding cutting elements that form a cage that self-centers within the blood vessel to reduce the risk of trauma to the vessel lining.

11 Claims, 4 Drawing Sheets

U.S. PATENT DOCUMENTS

| | | | |
|---|---|---|---|
| 4,955,375 A * | 9/1990 | Martinez | 128/207.15 |
| 5,112,301 A * | 5/1992 | Fenton et al. | 604/30 |
| 5,161,773 A * | 11/1992 | Tower | 251/5 |
| 5,180,364 A * | 1/1993 | Ginsburg | 604/510 |
| 5,197,192 A * | 3/1993 | Wylie et al. | 29/890.13 |
| 5,290,263 A * | 3/1994 | Wigness et al. | 604/247 |
| 5,295,956 A * | 3/1994 | Bales et al. | 604/30 |
| 5,305,982 A * | 4/1994 | Tamari | 251/5 |
| 5,314,406 A * | 5/1994 | Arias et al. | 604/21 |
| 5,374,244 A * | 12/1994 | Clement et al. | 604/32 |
| 5,376,100 A | 12/1994 | Lefebvre | |
| 5,441,482 A * | 8/1995 | Clague et al. | 604/35 |
| 5,464,398 A * | 11/1995 | Haindl | 604/523 |
| 5,527,292 A | 6/1996 | Adams et al. | |
| 5,549,626 A | 8/1996 | Miller et al. | |
| 5,584,803 A * | 12/1996 | Stevens et al. | 604/6.16 |
| 5,669,876 A * | 9/1997 | Schechter et al. | 128/898 |
| 5,827,243 A * | 10/1998 | Palestrant | 604/524 |
| 5,833,650 A | 11/1998 | Imran | |
| 5,935,100 A * | 8/1999 | Myers | 604/81 |
| 6,066,149 A * | 5/2000 | Samson et al. | 606/159 |
| 6,179,816 B1 | 1/2001 | Mottola et al. | |
| 6,251,121 B1 * | 6/2001 | Saadat | 606/180 |
| 6,450,987 B1 * | 9/2002 | Kramer | 604/43 |
| 6,468,291 B2 * | 10/2002 | Bates et al. | 606/200 |
| 6,540,712 B1 | 4/2003 | Parodi et al. | |
| 6,551,268 B1 * | 4/2003 | Kaganov et al. | 604/8 |
| 6,595,967 B2 * | 7/2003 | Kramer | 604/264 |
| 6,660,014 B2 | 12/2003 | Demarais et al. | |
| 6,855,136 B2 | 2/2005 | Dorros et al. | |
| 6,908,474 B2 | 6/2005 | Hogendijk et al. | |
| 7,223,253 B2 * | 5/2007 | Hogendijk | 604/6.12 |
| 2002/0103472 A1 | 8/2002 | Kramer | |
| 2002/0151918 A1 | 10/2002 | Lafontaine et al. | |
| 2004/0019310 A1 * | 1/2004 | Hogendijk | 604/1 |
| 2005/0020973 A1 * | 1/2005 | MacMahon et al. | 604/93.01 |
| 2005/0085761 A1 * | 4/2005 | Wang et al. | 604/6.11 |

FOREIGN PATENT DOCUMENTS

| | | |
|---|---|---|
| WO | 9823320 A1 | 6/1998 |
| WO | 0032264 A1 | 6/2000 |

* cited by examiner

EMBOLIC PROTECTION AND PLAQUE REMOVAL SYSTEM WITH CLOSED CIRCUIT ASPIRATION AND FILTERING

FIELD OF THE INVENTION

The present invention relates to methods and apparatus for aspirating a vessel to remove emboli liberated during an interventional procedure, and more specifically, a device that permits closed circuit filtering of blood aspirated from a treatment site.

BACKGROUND OF THE INVENTION

Average human life expectancy has been increasing over the past several decades. One result of this phenomenon is that an increasing number of patients require treatment for diseased vasculature, such as narrowing of the arteries due to plaque accumulation. Treatment of constricted arteries typically involves pre-dilating the vessel using an angioplasty balloon, followed by placing a stent in the vessel to retain the patency of the vessel. Often, pieces of the plaque break free from the vessel wall during the angioplasty procedure and/or stent placement, and pose a risk of blocking smaller downstream vessels, thus presenting a risk of infarction or stroke.

Several prior systems have been developed to capture emboli liberated during an interventional procedure such as angioplasty or stent delivery. Such systems generally seek either to capture the emboli using a filter disposed downstream of the treatment site, or a suction system configured to aspirate emboli-laden blood from the treatment site, or a combination of both.

For example, U.S. Pat. No. 5,549,626 to Miller et al. discloses a mesh-like filter basket that is deployed within the blood vessel to collect emboli liberated from the treatment site. Emboli first are captured in the basket and then aspirated from the vessel.

One disadvantage of the type of system described in Miller et al. is that the basket may become dislodged during the procedure, allowing the emboli to travel past the basket and pass into downstream circulation. Accordingly, it would be desirable to provide apparatus and methods for extracting emboli from a treatment site that do not involve deployment of a filter within the blood vessel.

U.S. Pat. No. 5,833,650 to Imran describes a multiple coaxial catheter system in which occlusion balloons are deployed proximal and distal to a lesion to define a treatment site. An intermediate balloon then may be advanced between the proximal and distal balloons to perform angioplasty, and any resulting emboli are aspirated from the treatment site using a suction pump. The aspirated blood is extracorporeally filtered and returned through a lumen of the innermost catheter to a location downstream of the distal balloon. The system described in Imran poses inherent risks associated with mechanically pumping blood from an occluded segment of vessel, e.g., such as vessel collapse. In addition, the use of multiple coaxial catheters limits the cross-sectional area of the lumen used to return blood to the patient's vasculature, leading to potential hemolysis, and limits the diameter of vessels in which the system practically may be employed.

U.S. Pat. No. 6,540,712 to Parodi et al. describes an alternative approach to embolic protection, in which emboli-laden blood is withdrawn from the treatment site using naturally-occurring pressure differentials. Withdrawn blood is extracorporeally filtered to remove the emboli and then the filtered blood is returned to the body via a connection the patient's venous vasculature. While that system has been proven to be highly effective at removing emboli, the use of a separate incision to place the venous return line has slowed its commercial adoption.

It therefore would be desirable to provide a system that enables blood to be withdrawn from the treatment site to be filtered, but which overcomes the drawbacks of previously known systems, such as the size limitations imposed by the multi-catheter arrangement of the Imran system or the need to provide multiple connections to the patient's circulatory system, as in the system of Parodi et al.

In addition, many rotational atherectomy devices are known in the art for removing plaque from within a vessel. For example, U.S. Pat. No. 5,376,100 to Lefebvre describes a device having a cylindrical member that expands radially when rotated at high speeds. Care must be taken when using the device to ensure that the cutting member does not contact the vessel wall and potential damage the vessel endothelium. U.S. Pat. No. 6,660,014 to Demarais, et al., also describes a rotating device deployed via catheter to the occlusion site, but with similar limitations.

It therefore would be desirable to provide a plaque removal device that reduces the risk posed by previously-known devices. In particular, it would be desirable to provide a plaque removal device that inherently self-centers within a vessel, so as to reduce the risk of damage to the vessel lining. In addition, it would be desirable to provide such a system having a minimum of mechanical complexity.

In view of the drawbacks of previously known methods and apparatus, it would be desirable to provide embolic protection apparatus and methods that allow emboli-laden blood to be removed from the treatment site, extracorporeally filtered, and returned to the patient's vasculature without multiple connections.

It also would be desirable to provide embolic protection apparatus and methods having bi-directional flow capability, while also preventing intermingling of filtered and unfiltered blood.

It further would be desirable to provide a plaque removal system for use with the proposed embolic protection apparatus, wherein the plaque removal system reduces the risk of damage to the vessel lining.

SUMMARY OF THE INVENTION

In view of the foregoing, it is an object of this invention to provide embolic protection apparatus and methods that allow emboli-laden blood to be removed from the treatment site, extracorporeally filtered, and returned to the patient's vasculature without multiple connections.

It is another object of the present invention to provide embolic protection apparatus and methods having bi-directional flow capability, while also preventing intermingling of filtered and unfiltered blood.

It is a further object of the present invention to provide a plaque removal system for use with the inventive embolic protection apparatus, wherein the plaque removal system reduces the risk of damage to the vessel lining.

It is another object of the present invention to provide a plaque removal system for use with the inventive embolic protection apparatus that can remove plaque from within the blood vessel and which is self centering within the vessel.

These and other objects of the present invention are accomplished by providing embolic protection apparatus and methods comprising a catheter having an occlusion element, a working lumen and a flexible liner disposed within the working lumen. The occlusion element is disposed on a distal end of the catheter and is configured to be deployed in a vessel proximal to a treatment site to arrest antegrade flow through the vessel. An actuator, which may comprise a syringe, is coupled to the proximal end of the catheter via inflow and outflow paths. Each of the inflow and outflow paths includes a one-way valve. A filter is disposed in the outflow path between the actuator and the catheter.

In accordance with the principles of the present invention, the catheter includes a first port that couples the working lumen to the inflow path, and a second port coupled to the outflow path. The flexible liner is disposed along the interior of the catheter and is movable between a first position, wherein the working lumen is coupled to the inflow path and serves as an inflow lumen, and a second position, wherein the flexible liner expands into the working lumen to define an outflow lumen. The flexible liner transitions between the first and second positions responsive to operation of the actuator.

During first mode of operation of the actuator, emboli-laden blood is withdrawn from the treatment site through the inflow lumen, first port and inflow path to the actuator. During a second mode of operation of the actuator, the emboli-laden blood is propelled from the actuator and through the outflow path and the filter. Filtered blood exiting the filter passes through the second port, and expands the flexible liner so that the blood flows through the outflow lumen and is reperfused in the patient's vessel at location proximal of the occlusion element. Accordingly, the removal of emboli-laden blood and reperfusion of filtered blood is accomplished using bi-directional flow through a catheter that is only negligibly larger than that employed in previously-known devices to provide a single blood flow path. Moreover, the apparatus of the present invention accomplishes bi-directional flow using only a single incision.

In accordance with another aspect of the present invention, a self-centering atherectomy device is provided to remove plaque from a treatment site within a vessel. The device comprises a plurality of self-expanding cutting elements that radiate from a central shaft. Deployed, these elements form a cage that may be rotated to abrade plaque from the interior of the vessel at the treatment site. In accordance with principles of the present invention, the cage is configured to be self-centering with the vessel, so as to reduce the risk of damage to the vessel lining.

Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference numerals refer to like parts throughout, and in which.

DETAILED DESCRIPTION OF THE INVENTION

The present invention is directed to embolic protection apparatus and methods comprising a catheter that provides closed circuit aspiration and filtering during an interventional procedure, such as angioplasty, atherectomy or stent delivery. The catheter is configured to occlude a blood vessel to arrest antegrade flow during the interventional procedure, and to aspirate emboli-laden blood from a treatment site, filter it, and reperfuse the filtered blood to the patient's vessel proximal to the occlusion element. Advantageously, the inventive apparatus permits filtration and reperfusion of blood to a patient with minimal blood loss and without requiring a separate access to enable reperfusion. A self-centering atherectomy device also is provided for use with the embolic protection apparatus.

Figure 1A:
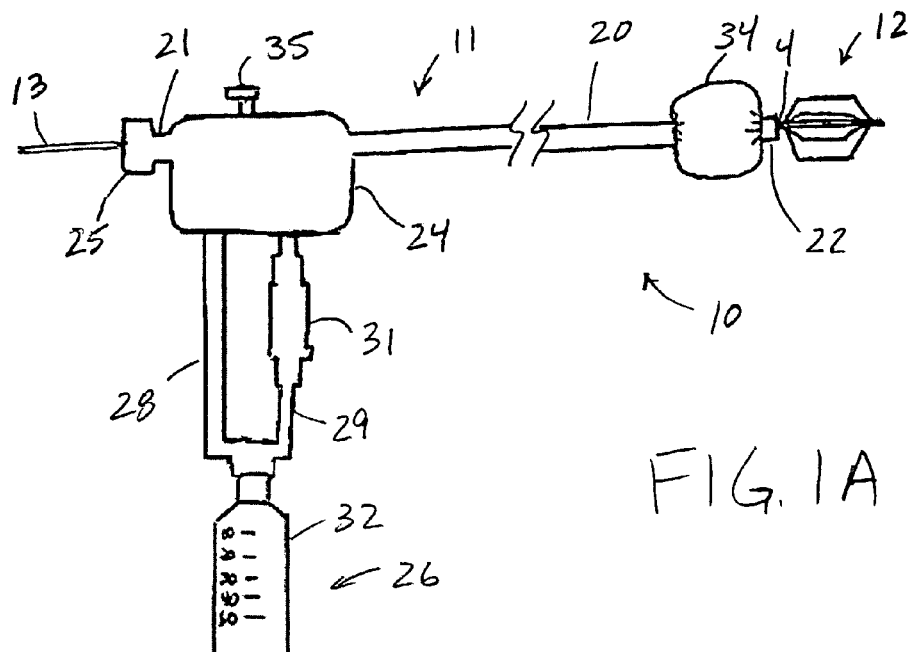
FIGS. 1A-1B are side and side sectional views of an embolic protection system constructed in accordance with principles of the present invention.
Figure 1B:
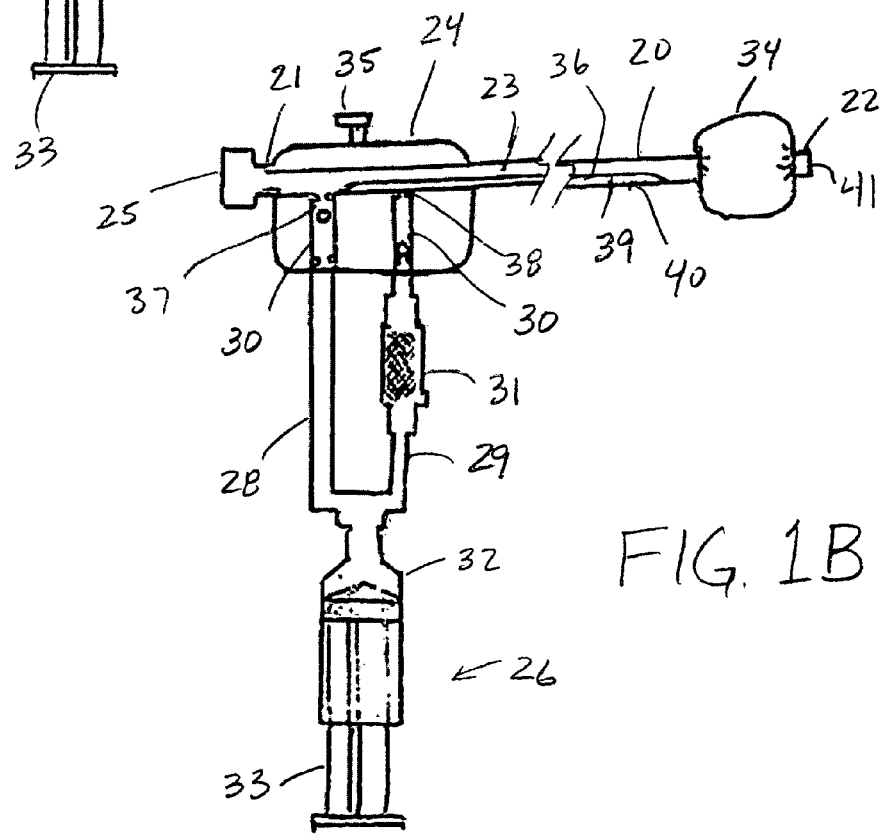

Referring to FIGS. 1A and 1B, embolic protection and plaque removal apparatus constructed in accordance with principles of the present invention is described. Apparatus 10 comprises aspiration device 11 and plaque removal device 12. Plaque removal device 12 is disposed through a working lumen of aspiration device 11 so that distal end 13 extends through a hemostatic valve 25 disposed on the proximal end of aspiration device 11 to permit manipulation of the plaque removal device.

Aspiration device 11 comprises catheter 20 having proximal end 21, distal end 22 and lumen 23 extending therebetween. Catheter 20 extends through manifold 24 and includes hemostatic valve 25 at proximal end 21. Manifold 24 is coupled to actuator 26 via inflow path 28 and outflow path 29, each of which includes one-way valve 30, such as a ball valve. Outflow path further includes filter 31 which is configured to filter emboli out of blood passing through the filter. Actuator 26 preferably comprises a syringe of conventional design and may comprise housing 32 and plunger 33.

Filter 31 may comprise any of a variety of blood filters which are known in the art, and preferably comprises at least one layer of biocompatible mesh that which allows blood to pass through, while capturing emboli. Preferably, filter 31 may be removably disposed in outflow path 29 so that debris collected in the filter may be analyzed.

Aspiration device 11 further comprises occlusion element 34 disposed near distal end 22 of catheter 20, inflation port 35 disposed on manifold 24, and an inflation lumen that couples occlusion element 34 to inflation port 35 to permit the occlusion element to be selectively inflated and deflated. Catheter 20 has flexible liner 36 disposed within lumen 23 along a portion of catheter 20 to selectively divide the lumen into inflow and outflow lumens, as described hereinafter.

Catheter 20 of aspiration device 11 preferably has a length suitable, e.g., 30 cm, for use in performing various interventional procedures, such as removal of plaque, angioplasty and/or stent delivery in the coronary, carotid or renal arteries. Aspiration device 11 preferably has an outer diameter suitable for passage through a conventional introducer sheath. Catheter 20 preferably is constructed of materials commonly used for catheter construction, such as polyurethane, PEBAX or nylon.

Figure 2A:
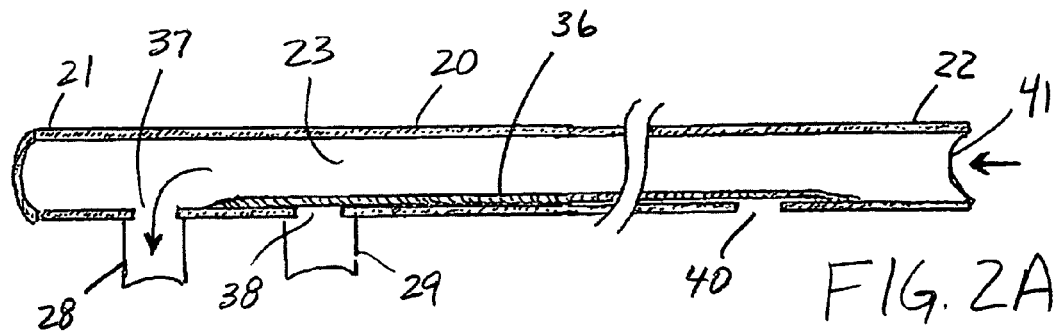
FIGS. 2A-2B are side sectional views depicting the flexible liner during aspiration of emboli-laden blood from the treatment site and reperfusion of filtered blood the patient's vessel, respectively.
Figure 2B:
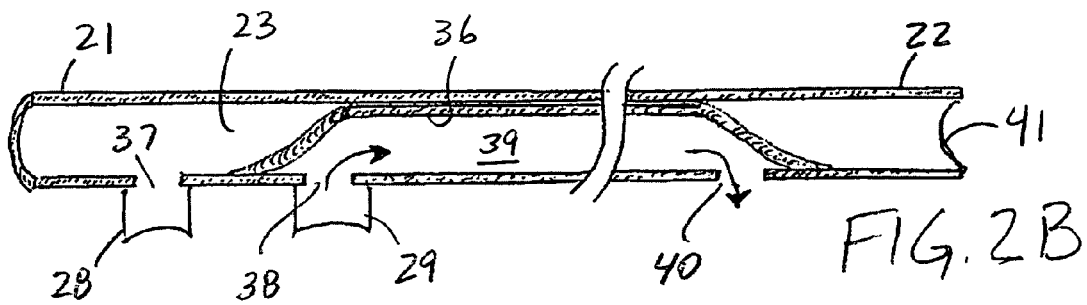

Referring now also to FIGS. 2A and 2B, which omits occlusion element 34 and its associated lumen for clarity, catheter 23 further includes first port 37 that permits lumen 23 to communicate with inflow path 28, and second port 38 that fluidly couples outflow path 29 to space 39 defined by flexible liner 36 and the interior wall of catheter 20. Catheter 20 has opening 40 disposed in the lateral face of the catheter at a location proximal of occlusion element 34; opening 40 is coupled to space 39 so that it is in fluid communication with second port 38.

Lumen 23 opens at distal end into distal port 41. Distal port 41 is configured to permit an interventional instrument, e.g., angioplasty balloon or atherectomy device, to be inserted through hemostatic port 25, advanced through lumen 23 and exit catheter through distal port 41 at a treatment site.

Flexible liner 36 is disposed along the interior of catheter 20 for a desired length of lumen 23 and is movable between first and second positions, responsive to operation of actuator 26. When liner 36 is in the first position, depicted in FIG. 2A, lumen 23 is coupled to first port 37 and inflow path 28 to serve as an inflow lumen. In the first position, liner 36 is collapsed against the interior wall of catheter 20 and lumen 23 provides fluid communication between distal port 41 and inflow path 28. With liner 36 in the first position, emboli-laden blood may be drawn through lumen 23 to actuator 26 as indicated by the arrows in FIG. 2A.

In the second position, depicted in FIG. 2B, liner 36 expands into lumen 23 to define space 39 that provides fluid communication between outflow path 29, second port 38 and opening 40. With liner 36 in the second position, emboli-laden blood may be expelled through the outflow lumen defined by space 39 from actuator 26 to opening 40, as indicated by the arrows in FIG. 2B.

Figures 3A, 3B, 3C:
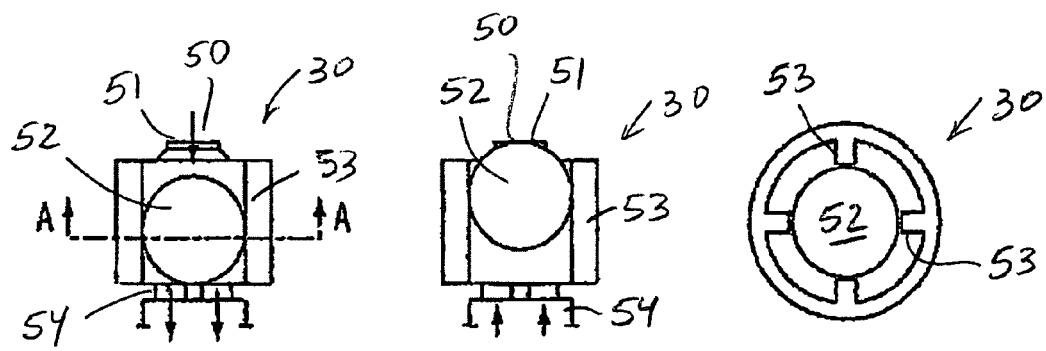
FIGS. 3A-3C are, respectively, side views of a one-way valve of the present invention in open and closed positions, and a cross-sectional view along line A-A of FIG. 3A.

With respect to FIGS. 3A-3C, an exemplary construction for one-way valve 30 is described. Each valve 30 preferably comprises valve inlet 50, seat 51, ball 52, guides 53 and outlet 54. Guides 53 permit ball 52 to move between an open position, wherein the ball is urged against seat 51 so that fluid can freely pass from inlet 50 to outlet 54, and a closed position, wherein the ball seats against inlet 50 to block flow through the valve. As will be appreciated, valves 30 are positioned in manifold 24 with reverse orientations, i.e., so that the valve on the inflow path opens when plunger 33 is withdrawn and seals when plunger 33 is compressed, while the valve on the outflow path operates in the reverse sequence.

During operation of aspiration device 11, plunger 33 of actuator 26 is withdrawn, causing the valve on inflow path 28 to open so that emboli-laden blood is drawn from the treatment site through lumen 23, first port 37 and inflow path 28 to housing 32. During this mode of operation, liner 36 is collapsed against the interior wall of catheter 20 and valve 30 on the outflow path is closed.

When plunger 33 is depressed, the valve on inflow path 28 closes, while the valve on the outflow path 29 opens. Plunger 33 expels the emboli-laden blood from housing 32 and through filter 31, thereby removing emboli from the blood. The filtered blood passes through second port 38 and causes liner 36 to expand into lumen 23. As plunger 33 is further compressed, filtered blood is expelled through the outflow lumen formed by space 39 and through opening 40 in the lateral face of catheter 20. Subsequent actuations of plunger 33 cause additional volumes of emboli-laden blood to be withdrawn from the treatment site, distal to occlusion element 34, filtered, and then reperfused in the patient's vessel at location proximal of the occlusion element.

Advantageously, the removal of emboli-laden blood and reperfusion of filtered blood is accomplished using bi-directional flow through a catheter that is only negligibly larger than that employed in previously-known devices to provide a single blood flow path. In addition, aspiration device 11 of the present invention accomplishes bi-directional flow using only a single connection to the patient's vessel.

The clinician may control the amount of suction applied during each cycle of plunger 33 by use of indicia on housing 32, which is preferably clear or opaque. In addition, the outflow path may include an auxiliary port to permit medication or a clot-reducing agent to be injected into the filtered blood before it is reperfused into the patient.

Figures 4A, 4B:
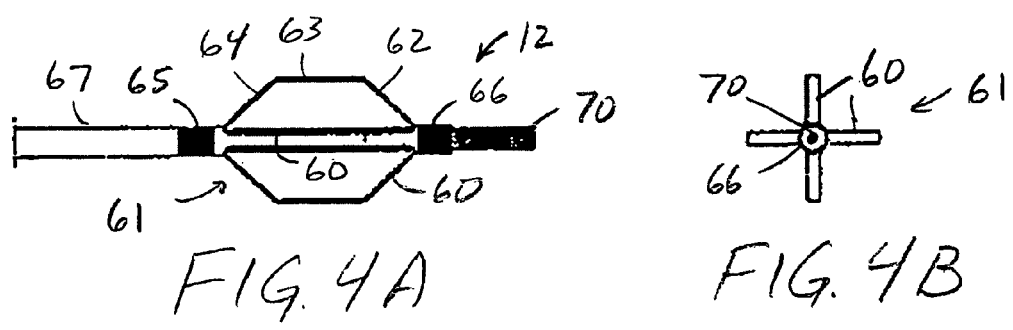
FIGS. 4A-4B are side and end views, respectively, depicting a cutter cage of the present invention suitable for use in removing plaque from a patient's vessel.

Referring now to FIGS. 4A and 4B, self-centering plaque removal device 12 suitable for use with the aspiration device 11 of the present invention is described. Device 12 preferably comprises a plurality of cutting elements 60, preferably ranging from two to eight in number, which together form cage 61. Each of cutting elements 60 has forward portion 62, central portion 63, and following portion 64. Preferably, cutting elements 60 comprise a nickel-titanium alloy or other shape-memory metal.

A rounded edge is provided on the wall-contacting portions of cutting elements 60 to reduce the risk of damage to the vessel wall as cage 61 is rotated. A sharpened or serrated edge also may be disposed on the leading edge of the cutting elements to increase the efficiency of plaque removal. In one preferred design, cutting elements 51 have a sharpened leading edge and a rounded trailing edge. Accordingly, cage 61 has different cutting characteristics depending on whether the device is rotated clockwise or counterclockwise.

Cutting elements 51 are joined at their proximal and distal ends, respectively, to proximal hub 65 and distal hub 66. Proximal hub 65 couples the proximal end of cage 61 to shaft 67. Shaft 67 has a guide wire lumen (not shown) that permits guide wire 70 to be inserted through shaft 66, proximal hub 65 and distal hub 67. Both proximal and distal hubs 65 and 66 may be provided with radiopaque markers. Shaft 67 is configured to extend through hemostatic port 25 of manifold 24 when cage 61 is deployed distal to occlusion element 34. In this manner, the clinician may manipulate the proximal end of shaft 66 to cause cage 61 to rotate. Because distal hub 65 is free to move axially along shaft 67, cage 61 may be collapsed for delivery through catheter 23.

Figure 5A:
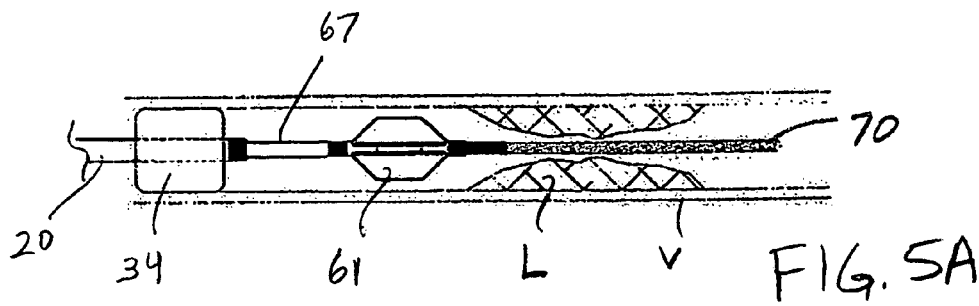
FIGS. 5A-5E are side views illustrating a preferred method of using the apparatus of FIG. 5.

Referring to FIGS. 5A-5E, a method of using plaque removal device 12 of the present invention to remove lesion L from within vessel V is described. In FIG. 5A, catheter 20 is disposed in vessel V just proximal to lesion L and occlusion element 34 is deployed to arrest antegrade flow through the vessel. Guide wire 70 then is advanced across the lesion, and plaque removal device 12 is deployed from through distal opening 41 of catheter 20 so that cage 61 is positioned just proximal of the lesion.

Figure 5B:
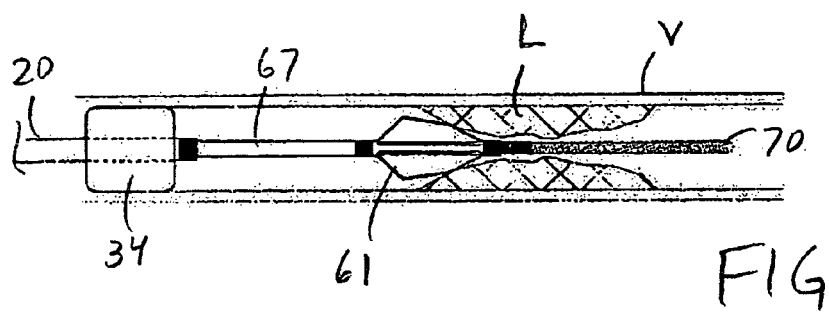

The clinician then rotates the proximal end of shaft 67, either by hand or by using a battery-operated motor, such as are known in the art of atherectomy. Using fluoroscopic visualization, the clinician advances the cage 61 while rotating it, as depicted in FIG. 5B. When cage 61 contacts lesion L, it begins to deform. Due to the shape-memory characteristics of cutting elements 60, cage 61 returns to its fully expanded state, thereby urging cutting elements 60 into continuous contact with lesion L.

Figure 5C:
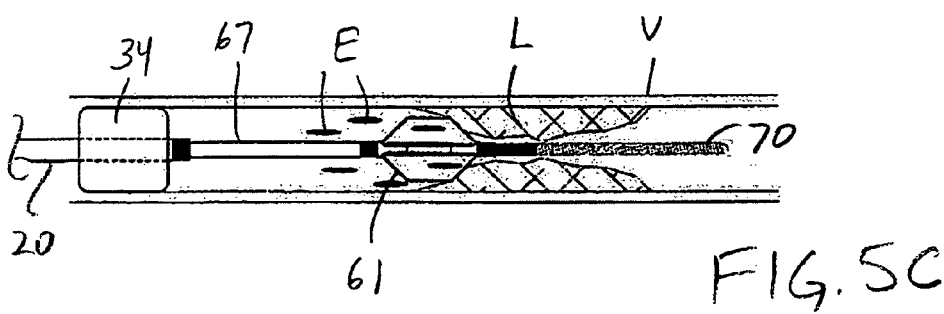
Figure 5D:
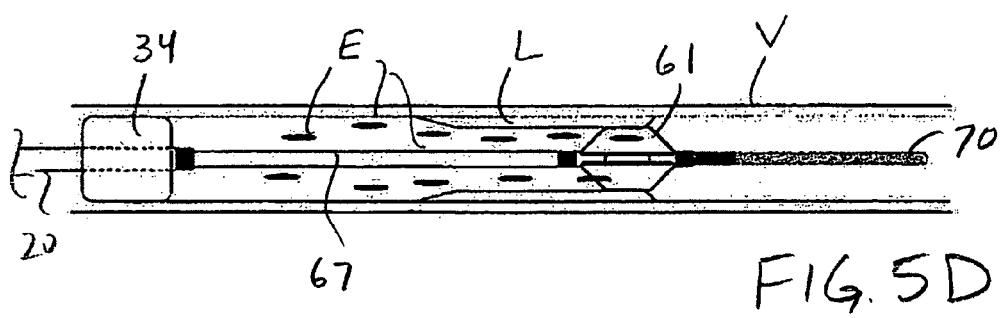
Figure 5E:
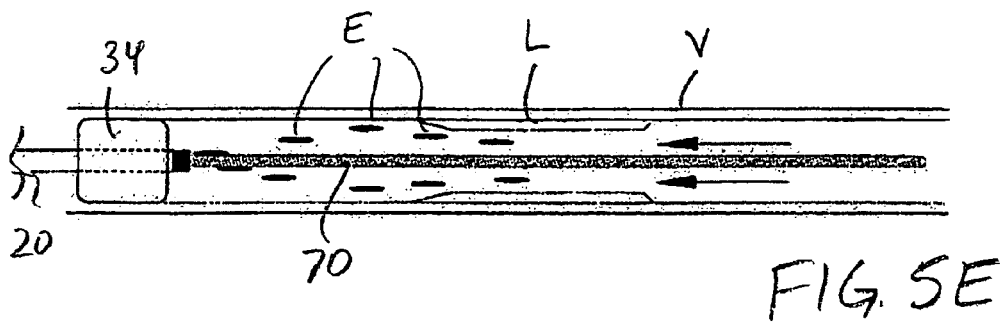

The clinician continues to rotate and advance cage 61 until the cage returns to its fully expanded state as shown in FIG. 5C. In this manner, cage 61 is advanced distally through lesion L until it clears a path through the lesion, as shown in FIG. 5D. After cage 61 completes cutting a path through the lesion, shaft 67 is retracted proximally, causing cage 61 to collapse and pass through lumen 23 of catheter 20, as depicted in FIG. 5E. At this point, the clinician may elect to repeat the plaque removal procedure with a cage having a larger diameter, or instead may deliver a stent to prevent restenosis of lesion L.

Throughout the procedure depicted in FIG. 5, emboli E are released into the vessel distal to occlusion element 34. In accordance with the present invention, the emboli-laden blood is aspirated from the treatment site through working lumen 23 of the catheter, as discussed above. The emboli then are filtered from the blood and the filtered blood returned to vessel V at a location proximal of the treatment site.

Figure 6A:
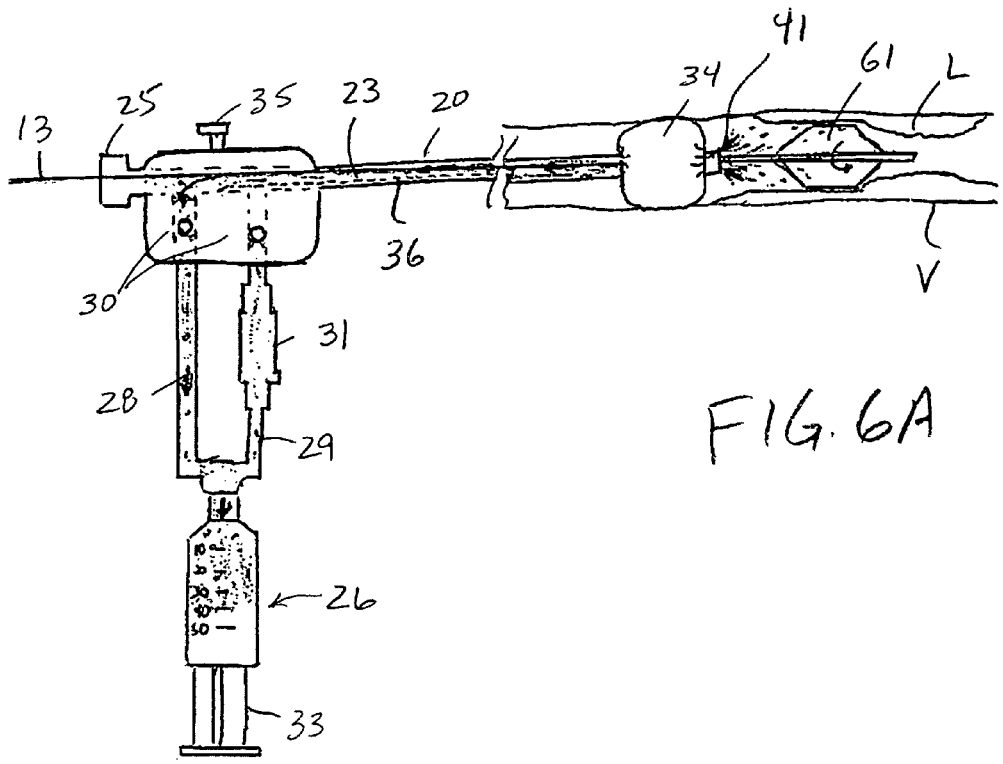
FIGS. 6A-6B illustrate a preferred method of using the apparatus of the present invention to remove plaque from a vessel while removing emboli generated during the plaque removal process.
Figure 6B:
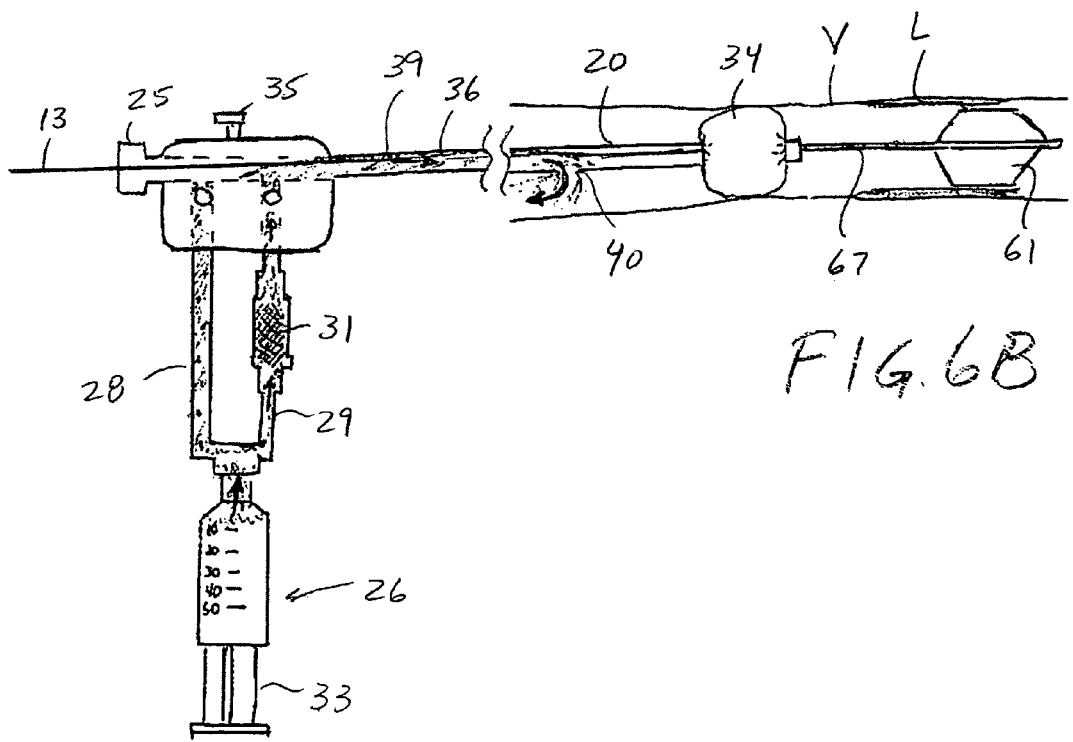

Referring to FIGS. 6A and 6B, a method of using aspiration device 11 and plaque removal device 12 together to remove a lesion from a vessel is described. The clinician first advances catheter 20 into the patient's vessel through a suitable introducer sheath and over a guide wire until distal end 22 of catheter 20 is located slightly proximal of the lesion, as determined using fluoroscopy or other known imaging modality.

Occlusion element 34 then is inflated via inflation port 35, halting antegrade blood flow, plaque removal device 12 is inserted over the guide wire as described above with respect to FIG. 5A. Operation of plaque removal device 12 then continues as described for FIGS. 5B through 5E. Progress of cage 61 may be monitored using fluoroscopy or other known imaging modality. During this procedure, the clinician may periodically stop cage 61 and aspirate blood and debris from the treatment site by operating actuator 26.

As discussed above, withdrawing plunger 33 of actuator 26 pulls blood through lumen 23 into housing 32 of the actuator, while depressing plunger 33 causes the blood to pass through filter 31 and be expelled through the outflow lumen and opening 40. Operation of the plaque removal device may then resume. In this manner, the clinician may periodically clear the vessel of debris, while maintaining some antegrade flow through the vessel during the procedure.

Upon completion of the plaque removal process, the clinician may again repeat the foregoing steps to ensure that any emboli or debris remaining at the treatment site have been collected and removed. Occlusion element 34 may then be deflated and the apparatus removed from the patient's vessel.

Although preferred illustrative embodiments of the present invention are described hereinabove, it will be evident to one skilled in the art that various changes and modifications may be made therein without departing from the invention. It is intended in the appended claims to cover all such changes and modifications that fall within the true spirit and scope of the invention.

What is claimed is:

1. Apparatus for removing emboli from a vessel during an interventional procedure, the apparatus comprising:
   a catheter having a proximal end, a distal end, a distal, blood inlet port at the distal end, and a lumen, the proximal end in fluid communication with the distal, blood inlet port via the lumen, the distal end configured for intravascular placement in the vessel;
   the catheter also having first and second ports and a third, blood outlet port, said first, second and third ports disposed between the proximal end and the distal end;
   an actuator comprising an actuator passageway, the actuator passageway comprising inflow and outflow paths, the actuator coupled to the catheter via the inflow path at the first port and the outflow path at the second port;
   a flexible liner disposed within the lumen of the catheter, the liner selectively movable between a first position collapsed against an interior surface of the catheter to occlude the second and the third ports while permitting aspiration of blood from the vessel, through the distal, blood inlet port, through the lumen, through the first port and into the inflow path, and a second position wherein the liner expands into the lumen to open the second and third ports and to create a space defining a return path connecting the second and third ports;
   the lumen, the actuator passageway and the return path defining a loop path;
   a filter disposed along the loop path; and
   whereby blood can flow in a first direction from the vessel, through the distal, blood inlet port, along the loop path, through the third, blood outlet port to be reperfused back into the blood vessel as filtered blood.

2. The apparatus of claim 1 further comprising a valve disposed in the inflow path or the outflow path.

3. The apparatus of claim 1 wherein the actuator comprises a syringe.

4. The apparatus of claim 1 further comprising a plaque removal device configured to be slidably advanced through the lumen of the catheter.

5. The apparatus of claim 1 in which the flexible liner is blood impermeable.

6. The apparatus of claim 1 wherein the filter is disposed along the outflow path.

7. The apparatus of claim 1 further comprising an occlusion element disposed adjacent the distal end.

8. The apparatus of claim 1 further comprising:
   a shaft having a guide wire lumen;
   a plurality of self-expanding cutting elements, the plurality of cutting elements having proximal ends coupled to a proximal hub and distal ends coupled to a distal hub to form a cage,
   wherein the cage self-centers when deployed in the vessel.

9. The apparatus of claim 8 wherein the cutting elements comprise a shape memory alloy.

10. The apparatus of claim 8 wherein a central section of each cutting element is disposed substantially parallel to a longitudinal axis of the shaft.

11. The apparatus of claim 1 further comprising valving, associated with the loop path, restricting blood flow along the loop path to flow in said first direction.

* * * * *